(12) United States Patent
Buehlmeier et al.

(10) Patent No.: US 7,548,312 B2
(45) Date of Patent: Jun. 16, 2009

(54) MEASURING DEVICE FOR INGREDIENT DETECTION

(75) Inventors: Robert Buehlmeier, Herzebrock-Clarholz (DE); Frank Claussen, Harsewinkel (DE); Christian Pfitzner, Harzgerode (DE); Andre Heinrich, Otterwisch (DE); Andi Guenther, Dresden (DE)

(73) Assignee: CLAAS Selbstfahrende Erntemaschinen GmbH, Harsewinkel (DE)

( * ) Notice: Subject to any disclaimer, the term of this patent is extended or adjusted under 35 U.S.C. 154(b) by 0 days.

(21) Appl. No.: 11/830,004

(22) Filed: Jul. 30, 2007

(65) Prior Publication Data

US 2008/0024760 A1 Jan. 31, 2008

(30) Foreign Application Priority Data

Jul. 31, 2006 (DE) ...................... 10 2006 035 906

(51) Int. Cl.
*G01J 3/42* (2006.01)
*G01N 21/35* (2006.01)

(52) U.S. Cl. ...................... 356/326; 356/323; 356/446; 250/339.07; 250/339.11
(58) Field of Classification Search ................ 356/326, 356/328
See application file for complete search history.

(56) References Cited

U.S. PATENT DOCUMENTS 3,874,799 A * 4/1975 Isaacs et al. ................ 356/402
4,661,711 A * 4/1987 Harjunmaa ............... 250/458.1

FOREIGN PATENT DOCUMENTS

DE 10 2004 021 448 11/2005
WO 99/40419 8/1999

* cited by examiner

*Primary Examiner*—F. L Evans
(74) *Attorney, Agent, or Firm*—Michael J. Striker

(57) ABSTRACT

A measuring device has a sensor for registering at least one parameter selected from the group consisting of at least one ingredient, at least one property, and both, of a material being investigated by the sensor, the sensor including at least one illumination source which directs at least one light beam toward the material to be investigated, at least one reference object for calibrating the measuring device, and an illumination source configured so that a portion of a light beam from the illumination source is redirected toward the reference object.

11 Claims, 4 Drawing Sheets

MEASURING DEVICE FOR INGREDIENT DETECTION

CROSS-REFERENCE TO A RELATED APPLICATION

The invention described and claimed hereinbelow is also described in German Patent Application DE 10 2006 035 906.2 filed on Jul. 31, 2006. This German Patent Application, whose subject matter is incorporated here by reference, provides the basis for a claim of priority of invention under 35 U.S.C. 119(a)-(d).

BACKGROUND OF THE INVENTION

The present invention relates to a measuring device with a sensor for detecting at least one ingredient and/or at least one property of a material being investigated by the sensor.

Publication DE 10 2004 021 448.4 makes known a spectrometric reflectance measuring head with internal recalibration. The housing of the measuring head contains two standards, preferably a black standard and a white standard for internal recalibration, which can be selectively swiveled into the beam path of the reflectance measuring head. After the spectrometer registers the measured data from both standards, the control and evaluation unit recalibrates the reflectance measuring head. In addition, at least two external standards can be provided to calibrate the reflectance measuring head before start-up of the measuring device or at certain time intervals. The at least two external standards are located in the beam path of the illumination source in place of the object to be measured.

The disadvantage of this known reflectance measuring head is that the standards used to calibrate the measuring device must be swiveled into the region of the beam path. This requires a swivel mechanism having a complex design, and the detection of crop material flow must be interrupted during the calibration procedure.

Publication EP 1 053 463 B1 makes known a combine harvester with a system for determining components of an agricultural crop material. The system includes a light source that illuminates the agricultural crop material, and a receiver for receiving the light energy reflected by the crop material. To calibrate the system, a motor is used to swivel a standard in front of the receiver, and a reference measurement is carried out. This system also has the disadvantage that a swivel mechanism with a complex design is required, and the detection of crop material must be interrupted during the calibration procedure.

SUMMARY OF THE INVENTION

The object of the present invention, therefore, is to avoid the disadvantages of the related art and, in particular, to provide a simple and, therefore, cost-favorable measuring device with which the material to be investigated and the reference object do not have to be switched back and forth.

In keeping with these objects and with others which will become apparent hereinafter, one feature of the present invention resides, briefly stated, in a measuring device, comprising a sensor for registering at least one parameter selected from the group consisting of at least one ingredient, at least one property, and both, of a material being investigated by said sensor, said sensor including at least one illumination source which directs at least one light beam toward the material to be investigated; at least one reference object for calibrating the measuring device; and an illumination source configured so that a portion of a light beam from said illumination source is redirected toward said reference object.

Given that a portion of the light beam from the illumination source is redirected to the reference object, there is no need for a mechanism that replaces the material to be investigated with the reference object, and the measurement of crop material flow takes place nearly continually, since there is no need to interrupt it for the swiveling procedure.

In a first inventive embodiment of the measuring device, a portion of the light beam from the illumination source is redirected by at least one reflector, thereby resulting in a simple, cost-favorable measuring device.

In a further inventive embodiment of the measuring device, the light beam from the illumination source is redirected by at least one prism, thereby also resulting in a cost-favorable measuring device with a simple design.

In a third inventive embodiment of the measuring device, a portion of the light beam from the illumination source is redirected such that it is guided by an optical waveguide, thereby allowing the reference object to be positioned anywhere with respect to the illumination source, without requiring a complex design.

Given that the material under investigation and/or the reference object reflect the light beam from the illumination source, and the light diffusely reflected by the material and/or the reference object is collected by at least one optical waveguide, and the optical waveguide guides the diffusely reflected light to a spectrometer, it is possible to position the spectrometer anywhere on the harvesting machine. In addition, further optical waveguides associated with further measuring devices on the harvesting machine can be connected with the spectrometer.

Given that the reference object includes a black standard and a white standard, the fluctuating light intensity of the illumination source and the change in sensitivity of the measuring device can be taken into account in the calibration, thereby preventing measured values from becoming corrupted.

Given that a multiplexer is installed upstream of the spectrometer—the multiplexer controlling which optical waveguide transmits the light to the spectrometer—it is possible to automatically switch between the measuring mode and calibration of the measuring device, and calibration takes place within milliseconds.

The fact that the spectrometer registers the measured data on the light diffusely reflected by the material under investigation and/or the reference object rules out the possibility that light reflected by the disk located between the illumination source and the crop material, for example, is also absorbed by the optical waveguides, which would result in incorrect measured data.

Given that the spectrometer is connected with a control and evaluation unit that calculates the content of ingredients and/or properties of the material under investigation, based on the measured data registered by the spectrometer, it is possible to analyze the material under investigation quickly and without destroying it.

The illumination source is advantageously designed as an infrared light source, since wavelengths in the near infrared range are optimally suited for detecting ingredients such as protein and the like in the material under investigation.

Advantageously, the material under investigation is a flowing stream of an agricultural product, thereby ensuring that a continual real-time measurement of a continually conveyed crop material flow can be carried out.

The measuring device is advantageously located on a harvesting machine, thereby enabling the analysis to be carried out while the crop material is being harvested with the harvesting machine.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
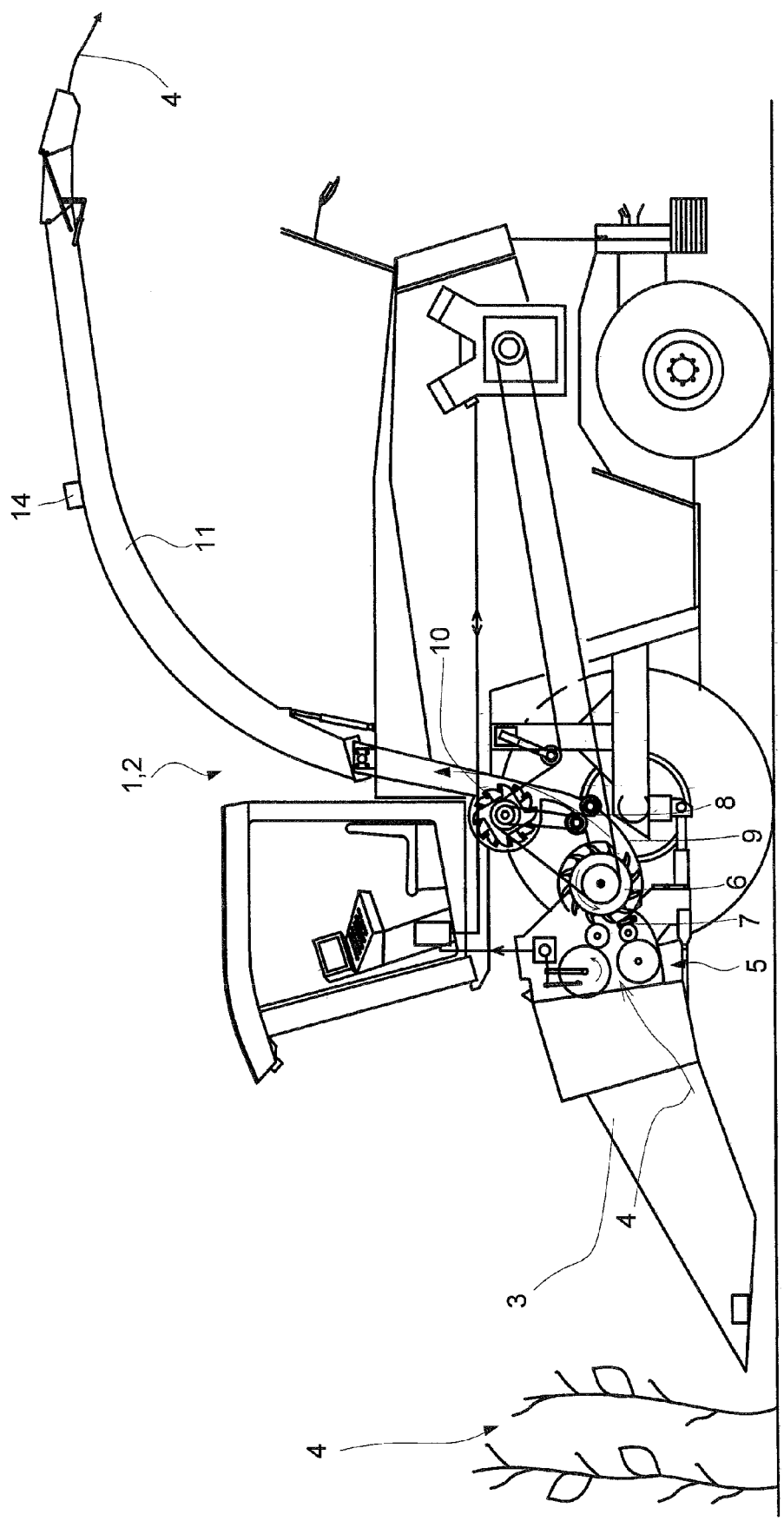
FIG. 1 shows a forage harvester in a side view, with an inventive measuring device.

FIG. 1 shows a side view, with a partial cross-sectional view, of an agricultural harvesting machine 2 designed as a self-propelled forage harvester 1. A front attachment 3 is assigned to the front, which picks up crop material 4 during the working operation of forage harvester 1, cuts it, then guides it to downstream, rotating intake and compression rollers 5. Intake and compression rollers 5 guide crop material 4 to downstream, rotating chopper drum 6, which fragmentizes crop material 4 in interaction with a shear bar 7. Fragmentized crop material 4 is transferred to a post-fragmentation device 8, which pounds the crop grains, e.g., corn, and transfers them via a conveyer chute 9 to a post-accelerator 10. Post-accelerator 10 accelerates fragmentized crop material 4 and conveys it—via a horizontally and vertically displaceable upper discharge chute 11—to a not-shown hauling device assigned to upper discharge chute 11.

Inventive measuring device 14—which will be described in greater detail, below—is located on upper discharge chute 11 in order to analyze crop material 4 being conveyed through the upper discharge chute.

It is also feasible to locate measuring device 14 on a feed channel of a baler or in the feed rake or the grain tank filling auger.

Measuring device 14 known per se is used to determine certain ingredients in crop material 4. Reference is made to EP 1 053 463 with regard for a more detailed determination of the ingredients; the teaching thereof is integrated in this full written disclosure via reference. Measuring device 14 registers the portions of ingredients in crop material 4, such as water content, or the content of raw protein or fat, and further parameters of crop material 4, such as fiber length, fiber content, and dry matter.

Figure 2:
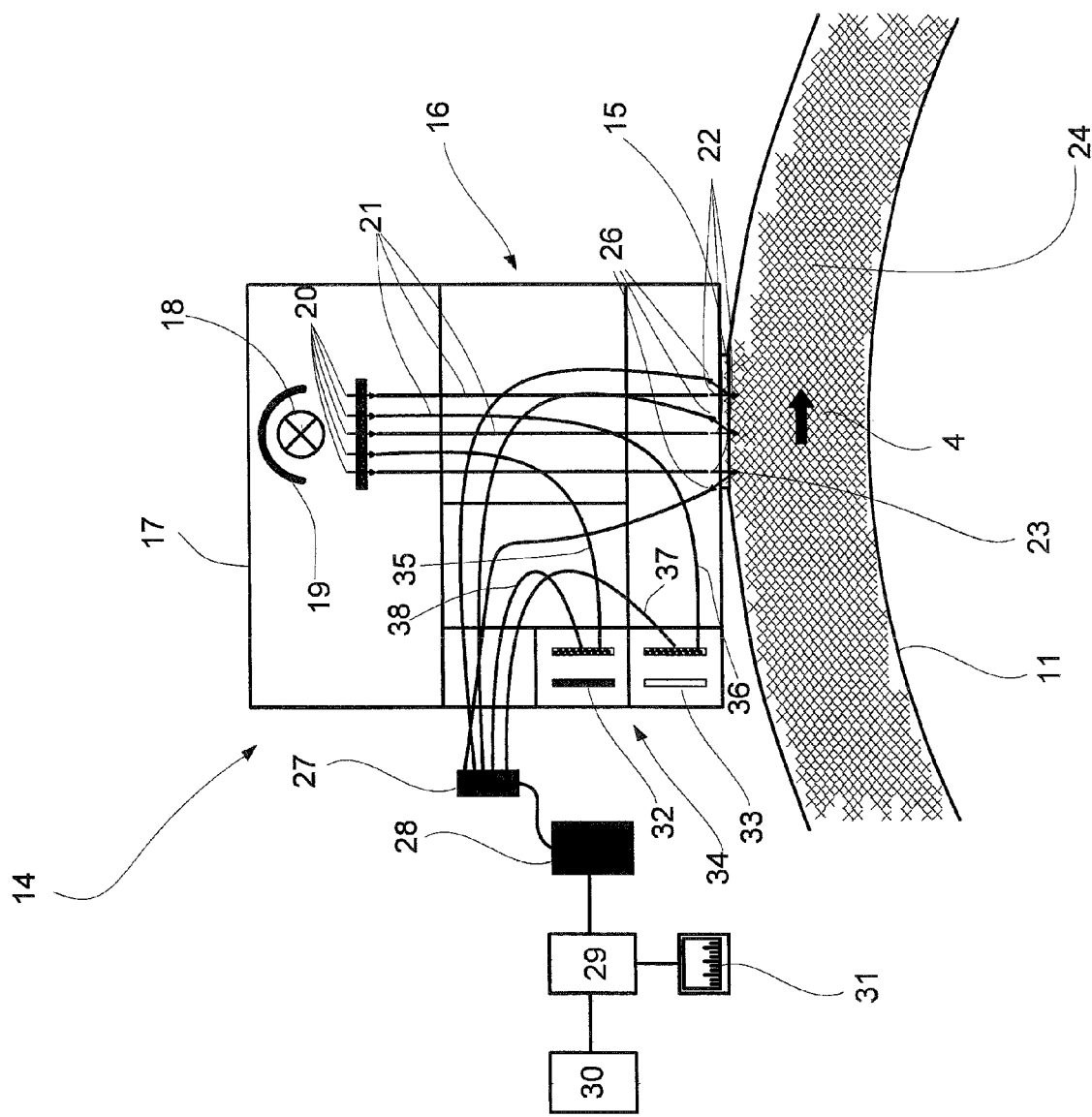
FIG. 2 shows a detailed depiction of the inventive measuring device.

FIG. 2 shows a detailed depiction of inventive measuring device 14 located on upper discharge chute 11. An opening 15 is provided in upper discharge chute 11, in the region of which measuring device 14 is located. Measuring device 14 includes a sensor 16, which is an optical sensor that operates in the reflectance mode.

Sensor 16 includes an illumination source 18 designed as an infrared light source and located inside housing 17, which emits a collimated light beam 20 downward, in the direction of upper discharge chute 11, using a parabolic mirror 19 located above illumination source 18. A portion of light beam 20 is collected by optical waveguides 21, which are also located in housing 17, and is guided toward upper discharge chute 11. Light beams 22 emerging from the lower end of optical waveguides 21 pass through a disk 23 of housing 17 located in the region of upper discharge chute 11 and into conveyor channel 24 of upper discharge chute 11, through which crop material 4 is conveyed. Light beams 22 are reflected diffusely by crop material 4. Further optical waveguides 25 are located inside housing 17, in order to collect a portion of diffusely reflected light 26. The ends of optical waveguides 25 are located at an angle of approximately 45 degrees relative to disk 23, to prevent light that is reflected by disk 23 from also being collected.

Optical waveguides 25 guide diffusely reflected light 26 via a multiplexer 27—which will be described in greater detail below—to a spectrometer 28. Spectrometer 28 registers—in a wavelength-specific manner—the spectrum of reflected light 26 and, therefore, the reflectivity of illuminated crop material 4.

Spectrometer 28 is connected with a control and evaluation unit 29, which calculates—based on signals provided by spectrometer 28, as described in greater detail in EP 1 053 463 B1 mentioned above—the contents of crop material 4 in terms of certain ingredients, such as water, starch, organic substances, non-organic substances, raw protein, oil, and the like . . . . The calculated values are transmitted to a fieldwork computer 30 that maps the values in a location-dependent manner. The values are also displayed in a display unit 31.

A reference object 34 that includes a black standard 32 and a white standard 33 is located inside housing 17; reference object 34 is used to calibrate measuring device 14 using a reference signal.

According to the present invention, in order to carry out a reference measurement, a portion of light beam 20 from illumination source 18 is redirected to reference object.

In the exemplary embodiment shown, the redirection takes place via curved optical waveguides 35, 36, each of which includes a first end, which points toward illumination source 18, and a second end, which points toward white standard 33 or black standard 32. Optical waveguides 35, 36 absorb a portion of light beam 20 from illumination source 18 and guide the collected light to standards 32, 33.

The light diffusely reflected by white standard or black standard is separated via first optical waveguide 36, and it is collected by a further optical waveguide 37 and sent to multiplexer 27.

Multiplexer 27 controls whether the light reflected by crop material 4—which is transmitted via optical waveguides 21 to multiplexer 27—or the light reflected by white standard 33—which is transmitted via optical waveguide 35 to multiplexer 27—or the light reflected by black standard 32—which is transmitted by optical waveguide 36 to multiplexer 27—is forwarded to spectrometer 28.

Before measuring device 14 is calibrated, multiplexer 27 forwards, in succession, the light reflected by white standard 33 and guided by optical waveguide 35, and the light reflected by black standard 32 and guided by optical waveguide 36 to spectrometer 28.

Spectrometer 28 forwards the measured data on standards 32, 33 to control and evaluation unit 29, which calibrates measuring device 14 using these measured data.

When determining the ingredients in a crop material 4, multiplexer 27 only forwards the light reflected by crop material 4—which is transmitted via optical waveguides 21 to multiplexer 27—to spectrometer 28.

The determination of the ingredients in crop material 4 must be halted in order to calibrate measuring device 14; in so doing, calibration is carried out within milliseconds and the ingredients in crop material 4 that is flowing past do not change substantially within this short period of time.

A further inventive measuring device 14 is possible, with which—in contrast to the design described above—the light reflected by white standard 33 and guided by optical waveguides 35, and the light reflected by black standard 32 and guided by optical waveguides 36 is directed to a first spectrometer, and the light reflected by crop material 4 is directed to a second spectrometer. This design has the advantage, in particular, that the investigation of crop material 4 can also be carried out permanently during the calibration measurements, since the light reflected by standards 32, 33, and the light reflected by crop material 4 can be evaluated independently of each other in separate spectrometers.

Figure 3:
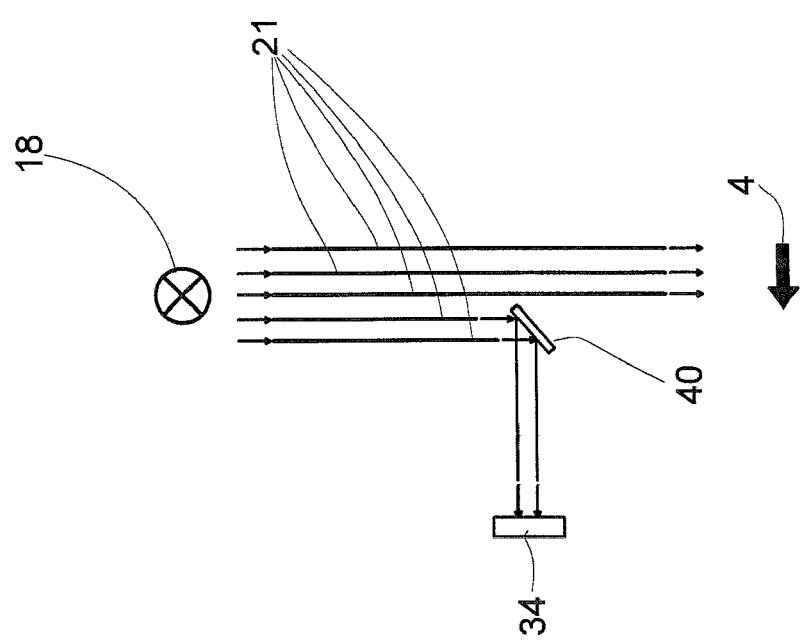
FIG. 3 shows an inventive measuring device with a reflector for redirecting the light beams.

FIG. 3 shows an inventive measuring device 14, with which a portion of light beams 21 from illumination source 18 directed at crop material 4 strikes reflector 40 positioned at an angle relative to light beams 21 and is redirected by reflector 40 to reference object 34.

Figure 4:
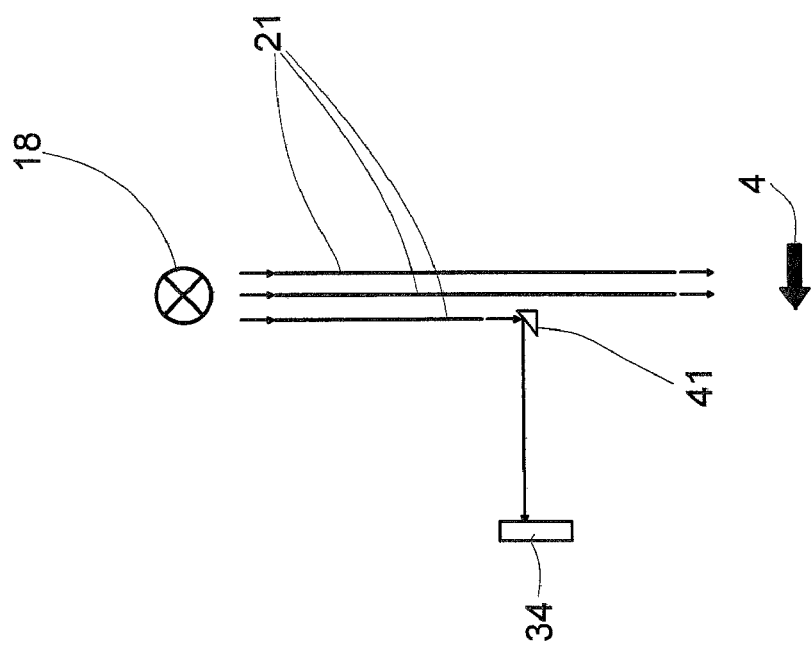
FIG. 4 shows an inventive measuring device with a prism for redirecting the light beams.

With inventive measuring device 14 shown in FIG. 4, a portion of light beams 21 from illumination source 18 directed at crop material 4 strikes a prism 41 and is redirected by prism 41 to reference object 34.

It is within the scope of the ability of one skilled in the art to modify the exemplary embodiments described in a manner not presented, or to use them in other machines to achieve the effects described, without leaving the framework of the invention.

It will be understood that each of the elements described above, or two or more together, may also find a useful application in other types of constructions differing from the type described above.

While the invention has been illustrated and described as embodied in a measuring device for ingredient detection, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A measuring device, comprising a sensor for registering at least one parameter selected from the group consisting of at least one ingredient, at least one property, and both, of a material being investigated by said sensor, said sensor including at least one illumination source which directs at least one light beam toward the material to be investigated; at least one reference object for calibrating the measuring device; and an illumination source configured so that a portion of the light beam from said illumination source is redirected toward said reference object, wherein said measuring device is configured so that said sensor registers at least one parameter of the material which is a flowing stream of an agricultural product.

2. A measuring device as defined in claim 1, further comprising at least one reflector which redirects said portion of the light beam from said illumination source.

3. A measuring device as defined in claim 1, and further comprising at least one prism which redirects said portion of the light beam from said illumination source.

4. A measuring device as defined in claim 1; and further comprising an optical waveguide, said illumination source being configured so that the portion of the light beam from said illumination source is redirected such that it is guided by said optical waveguide.

5. A measuring device as defined in claim 1; and further comprising a spectrometer; and an optical waveguide, so that the material under investigation and/or the reference object reflect a light beam from said illumination source, and a light that is diffusely reflected by the material and/or the reference object is collected by said at least one optical waveguide which guides the diffusely reflected light to said spectrometer.

6. A measuring device as defined in claim 1, wherein said reference object includes a black standard and a white standard.

7. A measuring device as defined in claim 5; and further comprising a multiplexer installed upstream of said spectrometer and controlling which optical waveguide transmits the light to said spectrometer.

8. A measuring device as defined in claim 5, wherein said spectrometer is configured so that it registers measured data on the light diffusely reflected by the material under investigation and/or the reference object.

9. A measuring device as defined in claim 5; and further comprising a control and evaluation unit which is connected with said spectrometer and calculates contents of ingredients and/or properties of the material under investigation, based on measured data registered by said spectrometer.

10. A measuring device as defined in claim 1, wherein said illumination source is an infrared light source.

11. A measuring device, comprising a sensor for registering at least one parameter selected from the group consisting of at least one ingredient, at least one property, and both, of a material being investigated by said sensor, said sensor including at least one illumination source which directs at least one light beam toward the material to be investigated; at least one reference object for calibrating the measuring device; and an illumination source configured so that a portion of the light beam from said illumination source is redirected toward said reference object, wherein said measuring device is configured so that it is locatable on a harvesting machine.

* * * * *